(12) United States Patent
Wolfrum

(10) Patent No.: US 6,225,068 B1
(45) Date of Patent: May 1, 2001

(54) PROCESS FOR SEQUENCING AN INDIVIDUAL DNA MOLECULE

(76) Inventor: Jürgen Wolfrum, 2 Südring, D-37124, Rosdorf (DE)

(*) Notice: Subject to any disclaimer, the term of this patent is extended or adjusted under 35 U.S.C. 154(b) by 0 days.

(21) Appl. No.: 09/509,579
(22) PCT Filed: Aug. 10, 1998
(86) PCT No.: PCT/EP98/05061
§ 371 Date: Jun. 13, 2000
§ 102(e) Date: Jun. 13, 2000
(87) PCT Pub. No.: WO99/15543
PCT Pub. Date: Apr. 1, 1999

(30) Foreign Application Priority Data

Sep. 25, 1997 (DE) .............................................. 197 42 227

(51) Int. Cl.[7] .................................................... C12Q 1/68
(52) U.S. Cl. .................... 435/6; 422/68.1; 422/82.07; 422/82.05; 422/82.08; 422/82.11; 436/164; 436/172; 436/532; 436/800; 436/805
(58) Field of Search ............................... 435/6; 422/68.1, 422/82.07, 82.05, 82.08, 82.11; 436/164, 172, 532, 800, 805

(56) References Cited

U.S. PATENT DOCUMENTS 5,401,469 * 3/1995 Kobayashi et al. ............... 422/82.07

* cited by examiner

*Primary Examiner*—W. Gary Jones
*Assistant Examiner*—Janell E. Taylor
(74) *Attorney, Agent, or Firm*—Blakely Sokoloff Taylor & Zafman

(57) ABSTRACT

An extended fibre point (1) is coated with photbiotin and irradiated with U.V. light, causing the photobiotin to bind with the fibre pint. The fibre point is then brounght into contact with streptavidin and submerged in a solution containing dyed copies of the DNA molecule to be sequenced. Biotin is also bonded to the 5' end of the dyed DNA molecules (4A). the biotin coupled to individual DNA molecules binds with the streptavidin at the fibre point. Light is coupled into the fibre to detect the thus obtained bonds. The evanescent field of said light excites a dyed DNA molecule to emit fluorescent light as soon as it binds with the fibre point. When a bond is deteccted, the fibre is immediately remvoded from the solution, and the fibre point is inserted into a microcapillary (5). The microcapillary is filled with a buffer solution containing exonucleases which decompose the DNA colecule base after base. The outlet (6) of the capillaries is located in the observation zone of individual molecule detection equipment. In order to improve the signal-noise ratio for individual molecule detection, the walls of the microcapillaries have a thickness in the area of their outlet which is distinctly smaller than ¼ the wavelenght of the exciting light.

19 Claims, 2 Drawing Sheets

PROCESS FOR SEQUENCING AN INDIVIDUAL DNA MOLECULE

The invention relates to methods in the sequencing of individual macromolecules, particularly individual DNA and RNA molecules.

For several years there have been attempts worldwide to sequence individual DNA molecules or strands. The sequencing of an individual DNA strand comprises the following steps:

a) Starting from the DNA molecule to be sequenced, the so-called template, which is present in a large number, DNA molecules are synthesised as complementary copies, in which dye molecules are coupled to at least some of the nucleotides. These DNA molecules are frequently designated as marked DNA. The synthesis takes place with the aid of a polymerase. As a result marked double strands are obtained or single strands, if required, after denaturing.

b) From the marked DNA strands one individual one is bonded onto a carrier.

c) The carrier is transferred into a detection apparatus; in the detection apparatus the individual partially marked nucleotides are broken down successively by an exonuclease, i.e. they are split off from the DNA strand.

d) The split-off and marked mononucleotides are detected and identified in the detection apparatus. This can be done with the aid of spectrally resolved or time-resolved fluorescence spectroscopy or other nucleotide-specific methods, such as for example mass spectrometry.

In the past step b) was carried out in such a way that microspherules with a diameter between 0.5 and 5 $\mu$m are coated with avidin or streptavidin. Biotin is coupled onto the 5' ends of the DNA strand. If the coated microspherules are dipped into a solution containing the biotinylated DNA strands, then the DNA strands bond onto the microspherules. If the concentration of the DNA strands in the solution is very small, then statistically only 0, 1, 2 or more DNA strands bond onto the spherules, but on average it is only between 0 and 1 DNA strand. With the aid of optical tweezers a microspherule is then sought which shows a fluorescence signal due to the bonded DNA strand. In this way a microspherule onto which precisely one DNA strand is bonded is found with a certain probability.

In order that the fluorescence of the DNA strand bonded onto the microspherule can be seen in spite of the Brownian movement of the microspherules, the DNA strand must be irradiated with a high-power excitation light. This can lead to a destruction of those dyes with which the DNA strand is dyed. In addition, the dye molecules in a highly-marked DNA strand fluoresce only poorly because of various fluorescence extinguishing processes.

The splitting off and detection of the mononucleotides in step d) frequently takes place in flow systems (J. Biomolecular Struc. & Dynamics, Volume 7 (1989) page 301). Due to a suitable construction of a flow system, the marked and split-off mononucleotides flow past a detection apparatus. This operates with a relatively large detection volume in the range of picoliters. The background signal is correspondingly great due to contaminants and Raman scattering. Furthermore, the flow system necessitates a relatively large distance between the collecting optical unit and the detection volume, as a result of which the collection efficiency drops.

The object of the invention is to improve the method for sequencing an individual DNA molecule.

In order to achieve this object, for the step b) of individual strand sequencing referred to in the introduction there is provided a method for extracting an individual fluorescible macromolecule from a fluid, this method being characterised in that a region of a tip of a fibre having a diameter of at most a few micrometers is coated with molecules, the molecules being selected so that they can form a bond with the material of the fibre tip and the fluorescible macromolecule;

that the coated fibre tip is dipped into the fluid containing the fluorescible macromolecule, so that the region of the fibre tip is irradiated with light of the excitation wavelength of the fluorescible macromolecule;

that the fluorescent light from the surroundings of the fibre tip is detected; and that the fibre tip is removed from the fluid as soon as the detected fluorescent light exceeds a predetermined intensity.

Due to the fact that a fibre with an extremely small tip is used, and also only a region of this tip is coated with molecules which can produce a bond between the fibre tip and the fluorescible macromolecule, there is only a very small surface onto which the fluorescible macromolecule can bond. Because the surface is so small, the probability that only one single molecule will bond onto the fibre tip is substantially increased.

Furthermore, on-line monitoring of the bonding of a fluorescible macromolecule onto the fibre tip is achieve. As soon as a predetermined increase in the intensity of the detected light is established, bonding of a fluorescible macromolecule onto the fibre tip can be assumed with a very high degree of probability. The fibre tip is then immediately removed from the fluid.

In the on-line monitoring a relatively long time is available for the fluorescence detection of the fluorescible macromolecule, which can no longer diffuse and which is bonded onto the fibre tip. Therefore the excitation intensity can be chosen to be correspondingly low. As a result, in turn, the probability of a photochemical destruction of the fluorescibility of the macromolecule is reduced.

If the concentration of the fluorescible macromolecule in the fluid is chosen in such a way that bonding onto the fibre tip occurs only at large time intervals, then the probability of two fluorescible macromolecules bonding simultaneously onto the fibre tip is very small. Consequently, when the fluorescent light exceeds a predetermined intensity the probability is very great that only one single fluorescible macromolecule has bonded onto the fibre tip.

The fluorescible macromolecule can be removed with the aid of the fibre tip from the fluid and transported to any other apparatus.

The given method for extracting an individual fluorescible macromolecule from a fluid is not restricted to DNA molecules. It can be used quite generally for any fluorescible macromolecule so long as a bond can be made between the macromolecules and the fibre tip. Also the method can be used both in gases and in fluids.

In an advantageous embodiment of the invention the coating of the fibre tip with molecules is achieved in that the surface of the fibre tip is coated with photobiotin molecules; that a spatially delimited region of the surface of the fibre tip is exposed to light in the wavelength range from approximately 300 to 360 nm in such a way that the photobiotin molecules are bonded onto the fibre tip in the irradiated region; that after this the unbonded photobiotin molecules are washed off from the fibre tip; and that the fibre tip is thereafter brought into contact with a solution containing avidin or streptavidin.

If biotin is bonded on the fluorescible macromolecule, then because of the strong bonding between biotin and avidin or streptavidin a coating of the fibre tip with these molecules suggests itself. This method constitutes a particularly elegant possibility of achieving a coating with avidin or streptavidin in the smallest possible region of the fibre tip. The coating of the fibre tip can be achieved by the use of focussed light in a region limited to fractions of a $\mu m^2$ terms of surface area. A fibre tip produced from glass or PMMA is pretreated in a known manner for the coating with photobiotin.

In an advantageous embodiment of the invention a dye-marked double-strand DNA molecule is extracted from an aqueous solution, wherein the aqueous solution has added to it intercalation dye molecules, the excitation wavelength of which lies in a different wavelength range from the excitation wavelength of the dye molecules. Light of the excitation wavelength of the intercalation dye molecules is input into the fibre and passed to the fibre tip in such a way that it has a small depth of penetration into the aqueous solution. The intercalation dye molecules are excited to fluorescence by the input light. The fluorescent light from the surroundings of the fibre tip is detected. The fibre tip is removed from the fluid as soon as the detected fluorescent light exceeds a predetermined intensity.

Thus it is no longer the dye molecules coupled onto the double-strand DNA molecule which are excited, but the intercalation dye molecules. Thus the dye molecules coupled onto the DNA are spared. They are crucial for later detection and identification of the individual nucleotides of the DNA molecule.

A further crucial aspect for success of single-strand DNA sequencing resides in the fact that so far as possible no marked and split-off nucleotide remains undetected.

For this purpose according to the invention a method is provided for detecting an individual fluorescible molecule in a fluid, in which a fluid is passed through a microcapillary which has at one end an outlet with an internal diameter between approximately 300 and 700 nm and has a wall thickness less than one quarter of the excitation wavelength of the fluorescible molecule, wherein the fluorescible molecule exits at the outlet;

a light beam of the excitation wavelength of the fluorescible molecule is focussed onto a region directly at the outlet of the microcapillary;

the fluorescent light is detected with a high collection efficiency; and the passage of the molecule through the focus is assumed as soon as the detected fluorescent light exceeds a predetermined intensity.

The split-off nucleotide leaving the capillary through the outlet produces a fluorescent light when it proceeds into the light beam shortly before, at or shortly behind the outlet.

The given method for detecting an individual fluorescible molecule is in no way limited to DNA molecules, but is applicable to any fluorescible molecules, e.g. fluorescent or fluorescence-marked proteins or amino acids. Because the relatively small outlet of the extended microcapillary is completely irradiated with light, no molecule can flow or diffuse past at the focus of the light source.

It is quite crucial for an improvement in the signal-to-noise ratio that the wall thickness of the extended microcapillary in the observed region is less than one quarter of the wavelength, preferably less than one eighth of the wavelength of the light used for excitation. As a result a greatly attenuated reflection of the excitation light occurs. This in turn leads to a marked reduction in the interfering background signal during the detection of an individual molecule.

A further attenuation of the reflection can be achieved in that the refractive index of the solvent filling the capillary tip and of the surrounding solvent is adapted to that of the glass material.

Charged fluorescible molecules, e.g. marked DNA molecules, nucleotides, amino acids, peptides, proteins, etc., can also be separated electrophoretically before leaving the microcapillary. For this purpose the microcapillary is dipped into a solution which is electrically coupled to an electrode. Within the microcapillary an electrical current path to a counter-electrode is formed by the solution. Between the electrode and the counter-electrode an electrical voltage difference is set up in such a way that the charged fluorescible molecules move out of the microcapillary through the end.

The object of the invention is further achieved by a method of sequencing an individual DNA molecule in which a) a plurality of substantially identical DNA molecules are synthesised in a solution, and in them dye molecules are coupled onto at least a part of the nucleotides (marked nucleotides);

b) one of the synthesised DNA molecules is extracted from the solution by bonding onto a fibre tip with a diameter of at most a few micrometers;

c1) the fibre tip is introduced into a microcapillary which has an internal diameter between approximately 300 and 700 nm at one end;

c2) the microcapillary is filled with a solution which effects a successive splitting off of individual nucleotides of the DNA molecule; and d) thereafter the individual split-off and marked nucleotides at the end of the microcapillary are detected and identified.

The bonding of the DNA molecule onto a fibre tip facilitates simple extraction thereof from the solution. Thus the bonded DNA molecule on the fibre tip can be introduced into a microcapillary. This is constructed so that it facilitates detection and identification of the marked mononucleotides.

Advantageous embodiments of the invention are characterised in subordinate claims.

The invention is explained in greater detail below with reference to embodiments which are illustrated schematically in the drawings. The same reference numerals in the individual Figures of the drawings denote the same elements. In detail in the drawings.

Production of Dyed DNA Molecules

If it is desired to decode the sequence of bases or of nucleotides of a DNA molecule on an individual DNA strand (sequencing), then first of all from the DNA strand to be sequenced a complementary copy (counter-strand) dyed with dye molecules must be synthesised.

This is achieved in that a short complementary DNA sequence, the so-called primer, is hybridised on to the 3' end of the DNA molecule (template) to be sequenced. D-biotin is coupled onto the 5' end of the primer. Nucleoside triphosphates are added to the solution in which the reaction for building up a complementary strand is carried out. Dye molecules are coupled onto these mononucleotides.

Until now it has not been possible to synthesise a counter-strand in which all nucleotides are dyed. In the past synthesis could only be carried out with in each case two of the four bases dyed. Thus dyed nucleoside triphosphates are added to the solution only for two of the four bases of the DNA. For the two other bases undyed nucleoside triphosphates are added to the solution. The actual copy of the template is then produced with the aid of a polymerase.

Extraction of an Individual DNA Molecule

As a rule the template will be present in a relatively large number, for example in micromolar concentration in solution. Accordingly many dyed copies of the template are produced. For single-strand sequencing an individual dyed DNA molecule must be extracted from the solution in the next step.

Figure 1A:
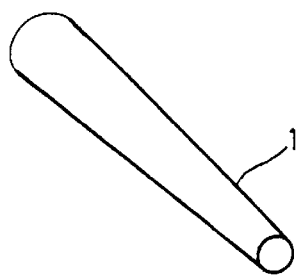
FIG. 1A shows a perspective view of a fibre tip.
Figure 1B:
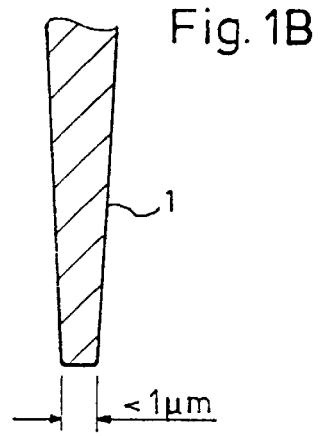
FIG. 1B shows a sectional view of a fibre tip.

For this purpose a fibre made from glass or PMMA is used, the tip of which has a diameter of less than 1 $\mu$m. Such a fibre tip is shown schematically in FIG. 1. The aim is, if possible, to bond only one single dyed DNA strand onto the fibre tip, biotin being bonded at the 5' end of the dyed DNA strands. Therefore it would be desirable to bond avidin or streptavidin on the smallest possible surface of the very small fibre tip which can bond biotin onto itself and thus facilitate bonding of the DNA strand onto the fibre.

In order to prepare the fibre in this way, first of all the glass or PMMA fibre is prepared in a known manner for the bonding of photobiotin. Then the fibre is dipped into a solution containing photobiotin. After it is removed, the fibre is irradiated with light of 300 to 360 nm wavelength from a laser beam focussed on the smallest possible region of the fibre tip.

As an alternative to focussing a light beam onto the tip, a SNOM tip can be used as fibre tip (SNOM=Scanning Nearfield Optical Microscopy). Light with a wavelength between 300 and 360 nm is input into this from the end remote from the tip. It exits exclusively at the fibre tip. Only there is the photobiotin then exposed to light.

By exposure of the photobiotin to light of the stated wavelengths a bond is produced between the photobiotin and the surface of the glass or PMMA fibre prepared in the known manner. After the exposure to light the unbonded photobiotin is removed from the fibre in a washing stage.

Figure 2A:
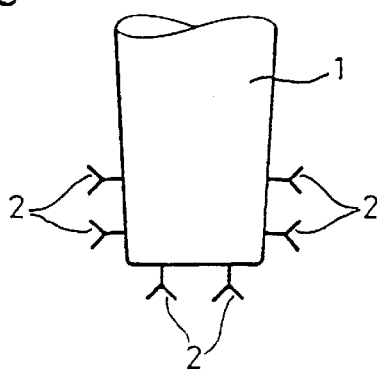
FIG. 2A shows a schematic representation of a fibre tip coated with avidin.

The fibre tip is then dipped into a solution containing avidin or streptavidin. Avidin or streptavidin has four bonding points for biotin. Thus it bonds onto the biotin which is immobilised on the fibre. Its other three bonding points remain free and can bond onto the biotin coupled onto the DNA strands. FIG. 2A shows schematically the fibre tip 1 with avidin molecules 2 on it.

Thus as a result a fibre tip is obtained on which avidin or streptavidin is bonded in a very small region of a few 100 nm diameter.

Figure 2B:
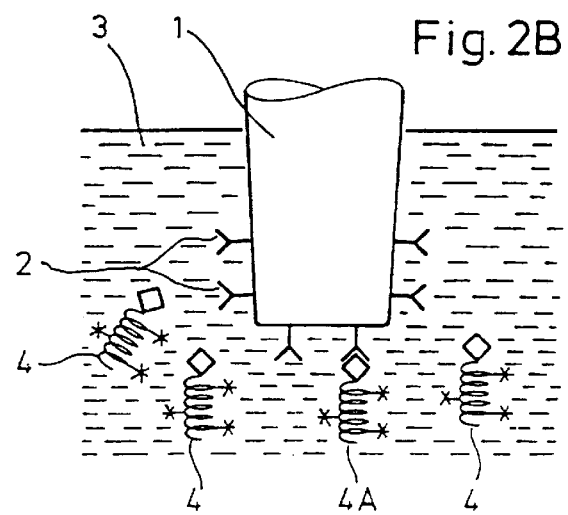
FIG. 2B shows a schematic representation of the boding of biotinylated and dye-marked DNA onto the coated fibre tip according to FIG. 2A.

In the next step the fibre 1 prepared in this way is dipped into the solution 3 in which the biotinylated and dyed DNA strands 4 are contained, as is shown in FIG. 2B. The aim is to detect the bonding on of an individual DNA strand or of the DNA strand (4A) onto the fibre tip 1 as immediately as possible with the aid of fluorescence spectroscopy. For this purposes two optical detection methods suggest themselves which can be combined with three DNA marking possibilities.

In the first optical detection method for detecting the coupling of an individual DNA molecule onto the fibre tip, the solution 3 with the dyed and biotinylated DNA strands 4 is located in an observation volume of a confocal construction or of a fluorescence microscope. Light is input into the fibre 1 in such a way that it is passed through the fibre to the tip thereof. The light exits evanescently in the region of the tip, i.e. its depth of penetration into the solution is limited to a few 100 nm. If a biotinylated and dyed DNA molecule now bonds onto the surface of the fibre, then it enters the region irradiated by the light in the vicinity of the surface of the fibre. There it is excited to fluorescence. This can be demonstrated in the fluorescence microscope. Thus it is established that a DNA strand has bonded onto the fibre. Thereupon the fibre is removed from the solution without delay.

The second optical detection method makes use of the fact that a part of the fluorescent light emitted by the dye molecules of the bonded DNA molecule is input back into the fibre. This can be detected at the end of the fibre opposite the fibre tip.

The concentration of the biotinylated and dyed DNA strands in the solution should be chosen during extraction to be so low that bonding of a DNA strand only takes place at very great time intervals. As a result the certainty increases that in the event of an observed increase in the signal brought about by the fluorescent light only one single DNA strand has bonded onto the fibre.

Since the DNA strands bonded onto the fibre tip no longer diffuse in the solution, a relatively long time is available for their detection, i.e. the detection of the fluorescent radiation emanating from them. The intensity of the excitation light input into the fibre can be chosen to be correspondingly lower. It is possible to operate here with an intensity of approximately 1 MW/cm$^2$ which is lower than usual for detection of an individual molecule by a factor of 100.

A pulsed diode laser with a wavelength in the red spectral range at approximately 640 nm is chosen typically as excitation light source. Diode lasers operate very reliably and are extraordinarily economical and compact. During operation in the red spectral range many interfering background signals are strongly suppressed. The use of a pulsed diode laser is advantageous when the nucleotides are to be identified on the basis of the fluorescent lifetime of the dye molecules coupled onto them.

Other lasers or other light sources can also be used. Many aspects of the invention can also be carried out without pulsed lasers, i.e. with continuous-wave lasers or light sources.

The first possibility for marking a DNA molecule is the marking of a DNA double strand as described above by the inclusion of dyed nucleotides.

A second possibility for DNA marking resides in the fact that an intercalation dye is previously added to the solution from which the DNA molecule is to be extracted. The excitation wavelength of this intercalation dye should deviate markedly from that of the dyes which have been used for marking the nucleotides. Then in order to demonstrate the bonding of the DNA molecule onto the fibre tip light is used with a wavelength at which damage to the dyes can be avoided. The intercalation dye Picogreen from the firm Molecular Probes is suitable, for example. It absorbs at 490 nm and emits at 520 nm. On the other hand, the dyes used for marking the nucleotides absorb at the wavelength of the diode laser, i.e. at approximately 640 nm.

For excitation of the intercalation dyes coupled onto the DNA molecules a laser beam is input in the manner already described into the fibre from the end remote from the extended tip. The detection of the fluorescent light of the intercalation dye can in turn be carried out using the two detection methods described above.

Then the double-strand DNA is denatured in ethanol. As a result the intercalation dyes are released again from the DNA. Also the DNA is released in individual strands, the unmarked template being released from the fibre tip. For the following exonucleolytic breakdown of the individual nucleotides of the marked DNA strand an exonuclease is then used which is capable of breaking down individual DNA strands.

A third possibility for DNA marking for observation of the bonding of a DNA molecule onto the fibre tip consists of providing the 3' end of the marked DNA with an additional marker. In this case B-phycoerythrin or dyed microspherules are considered as markers. These can be coupled enzymatically or chemically onto the 3' end of the DNA molecules.

Here too the excitation wavelength of the additional marker should preferably lie in a different wavelength range from the excitation wavelength of the dyes used for marking of the nucleotides.

In one embodiment, after the extraction of a DNA molecule, i.e. after the extraction of the fibre tip from the solution, the bonding of a DNA molecule onto the fibre tip is checked. For this purpose the fibre tip can for example be brought into the focussing range of a confocal fluorescence scanning microscope. Bonded DNA molecules can be easily detected there.

Detection of the Sequence of the Nucleotides of a DNA

Figure 3:
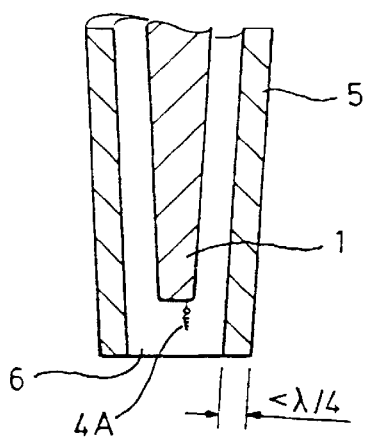
FIG. 3 shows a sectional view of an arrangement of a fibre tip with a DNA molecule bonded thereon in an extended microcapillary.
Figure 4:
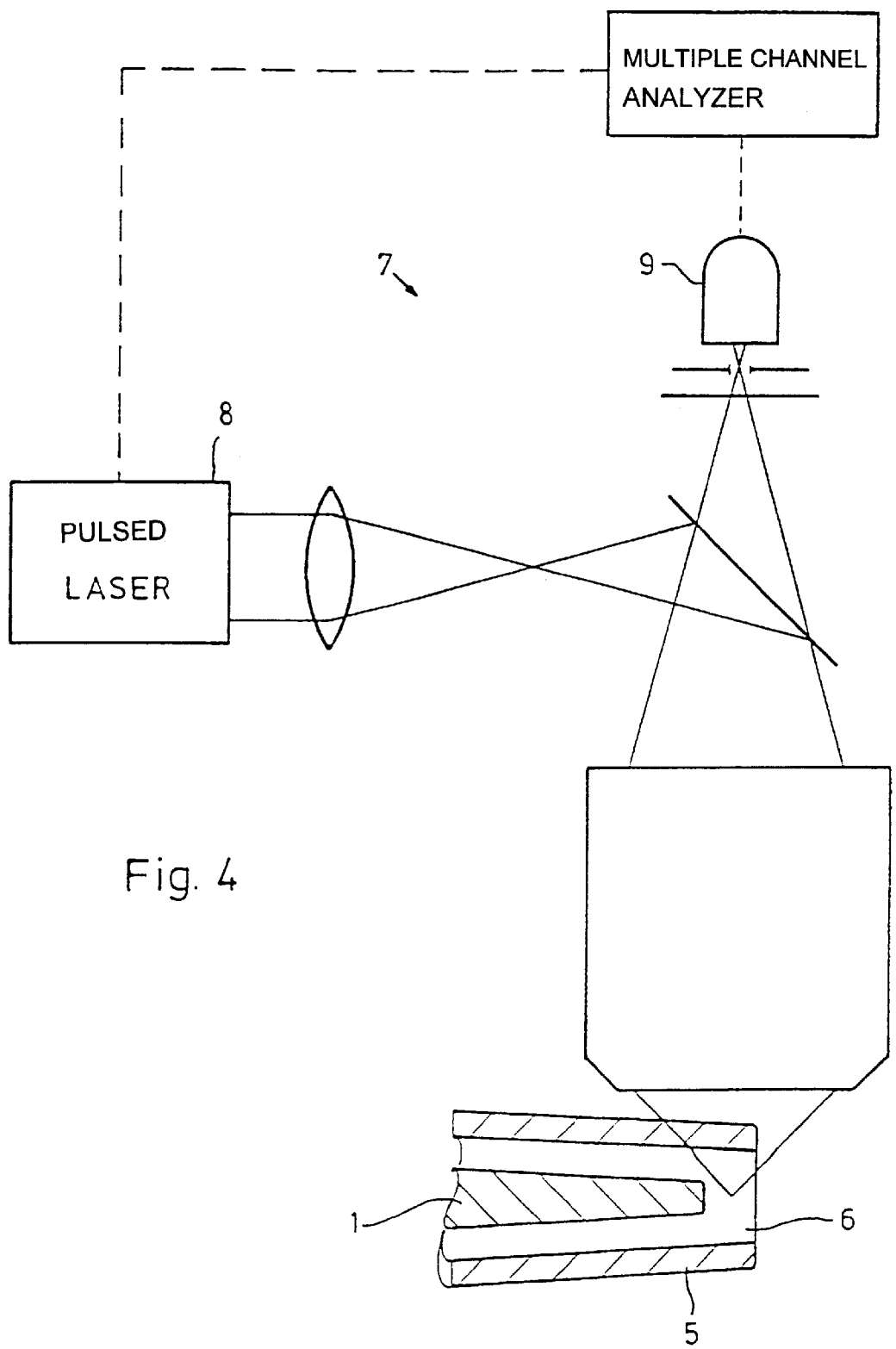
FIG. 4 shows a schematic representation of the arrangement according to the invention.

The fibre tip 1 on which precisely one DNA molecule 4A is bonded is introduced into an extended microcapillary 5, as is shown in FIG. 3. Such capillaries are obtainable as microinjection capillaries for biological applications. They have at the extended end an internal diameter of approximately 500±200 nm and a wall thickness of approximately 100 nm. The fibre tip is positioned in the microcapillary in such a way that the DNA molecule is only a few $\mu$ m away from the outlet of the microcapillary.

The microinjection capillaries also have a thread on their broad end so that they can be easily mounted on highly precise positioners.

The microcapillary is then charged with a buffer solution which contains all the substances necessary for the breakdown of the DNA strand, also including the exonucleases. These successively release the nucleotides from the DNA strand.

In order that the split-off nucleotides can be detected and identified, they must transported to the outlet 6 of the microcapillary 5. For this purpose the capillary 5 is dipped into a buffer solution in which an electrode is located. A corresponding counter-electrode is disposed in the end of the microcapillary remote from the extended tip. Between the electrode and the counter-electrode a voltage is applied which causes an electrical field in the solution which, depending upon the chemical treatment of the internal walls of the capillary and the chosen buffer system, is adjusted in such a way that the split-off mononucleotides are drawn into the buffer through the outlet of the microcapillary.

A confocal fluorescence detection system 7 observes the region of the outlet 6 of the microcapillary 5, for example immediately in front of the outlet inside or outside the microcapillary. The light of the pulsed diode laser 8 is focussed onto this region. The focus diameter amounts to somewhat less than 1 $\mu$m. The internal diameter of the microcapillary at the extended end amounts to approximately 500 nm. Thus the entire region of the outlet of the microcapillary is irradiated by the laser. The light collecting optical unit of the confocal construction is aligned so that it likewise detects the entire region, which is referred to below as the test area.

If a split-off mononucleotide moves from the fibre tip 1 to the outlet, then it crosses the focussing range of the detection means. The dye-marked mononucleotide is then excited to fluorescence in a known manner. The individual fluorescent photons emitted by the dye coupled onto the mononucleotide are detected on a single photon detector 9. The detector is coupled in a known manner to a signal processing means in order to facilitate time-correlated counting of single photons.

In the detection of individual molecules which is necessary here it is crucial for a good signal-to-noise ratio that the walls of the microcapillary in the test area, i.e. in the region just in front of the outlet, have a wall thickness which is less than the wavelength of the light used for excitation, preferably markedly less than one quarter of the excitation wavelength, i.e. at most approximately 100 nm. As a result a strongly attenuated reflection of the excitation light occurs on the walls. This markedly reduces the signal-to-noise ratio. Consequently the signal-to-noise ratio increases for the detection of individual molecules.

A crucial advantage which results from the very close placing of the fibre tip with the bonded DNA molecule at the outlet resides in the drastic reduction in the probability that a mononucleotide is lost by absorption on the inner wall of the microcapillary on the way from the fibre tip to the outlet. Thus it is possible to detect the individual marked and split-off mononucleotides.

There are various ways in which the individual mononucleotides can also be identified after detection. For example one dye molecule with a special emission wavelength can be chosen for each type of nucleotide. In the embodiment considered here, the different types of nucleotide are marked with dyes which have similar absorption and emission wavelengths but which each have different fluorescent lifetimes. The fluorescent lifetimes of the individual detected mononucleotides can be identified with sufficient reliability by the excitation of the dyes in the test area with pulsed laser light and the detection of the photons emitted from the test area by means of time-correlated counting of single photons. Thus an identification of the individual mononucleotides can be carried out with corresponding reliability.

Thus the aim of sequencing a DNA strand would be achieved if all nucleotides were marked selectively with dyes with differing fluorescent lifetimes. Since this has not been possible hitherto, only two different nucleotides in each case are marked with in each case two dyes with differing fluorescent lifetimes. The sequencing of the DNA strand is then repeated, but other bases are marked with dyes, until a sufficient reconstruction of the sequence of the template is possible.

What is claimed is:

1. A method for extracting an individual fluorescible macro-molecule from a fluid, said fluorescible macromolecule having an excitation wavelength, said method comprising the steps of coating a region of a tip of a fiber with molecules, said molecules being able to form a bond with the material of the fiber tip and with the fluorescible macromolecule;

dipping the coated fiber tip into the fluid containing the fluorescibel macromolecule, whereby said region of the fiber tip is irradiated with light of said excitation wavelength of the fluorescibel macromolecule;

detecting fluorescent light from the surroundings of the fiber tip; and removing the fiber tip from the fluid as soon as the detected fluorescent light exceeds a predetermined intensity.

2. The method as claimed in claim 1, wherein the region of the fiber tip is irradiated with light of said excitation wavelength of the fluorescible macromolecule by introducing the light into the fiber and passing it through the internal part of the fiber to the fiber tip in such a way that an evanescent field is produced at said region.

3. The method as claimed in claim 1, wherein the region of the fiber tip is irradiated with light of said excitation wavelength of the fluorescible macromolecule by bringing the fiber tip into the focusing range of a microscope, and wherein by means of fluorescence microscopy it is checked whether a fluorescible macromolecule is bound onto the fiber tip.

4. The method as claimed in claim 1, wherein the tip of the fiber has a diameter of less than 1 μm.

5. The method as claimed in claim 1, wherein biotin is bound onto the fluorescible macromolecule; and wherein avidin or streptavidin are used as molecules for the coating of the fiber tip.

6. The method as claimed in claim 5, wherein said region of the fiber tip is coated with avidin or streptavidin by coating the fiber tip with photobiotin molecules;

said region of the surface of the fiber tip is exposed to light in a wavelength range from approximately 300 to 360 nm so that the photobiotin molecules are bound onto the fiber tip in the region exposed to the light;

the unbound photobiotin molecule are washed off the fiber tip; and in that the fiber tip is dipped into a solution containing avidin or streptavidin.

7. The method as claimed in claim 5, wherein a DNA or RNA molecule is used as fluorescible macromolecule;

biotin is coupled onto the 5' of the DNA or RNA molecule;

before the dipping of the fiber tip an additional marker molecule is coupled to the 3' end of the DNA or RNA molecule, the excitation wavelength of this additional marker molecule lying in a wavelength range different from the excitation wavelength of a dye marking the nucleotides of the DNA or RNA molecules; and wherein light of the excitation wavelength of the additional marker molecule is input into the fiber and passed to the fiber tip.

8. The method as claimed in claim 1, wherein the fluorescent light from the surroundings of the fiber tip is detected by passing the fluorescible light emitted by the fluorescibel molecule near the fiber tip through the fiber and detecting the fluorescent light at an end of the fiber opposite to said fiber tip.

9. The method as claimed in claim 1, wherein a dye-marked double-strand DNA molecule is extracted from an aqueous solution, before the dipping of the fiber tip the aqueous solution has added to it intercalation dye molecules, the excitation wavelength of which lies in a different wavelength range from the excitation wavelength of the dye marking the DNA molecule;

light of the excitation wavelength of the intercalation dye molecules is input into the fiber and passed through the internal part of the fiber to the fiber tip; and wherein after the dipping the light is passed in the fiber in such a way that an evanescent field is produced at said region.

10. A method for sequencing an individual DNA molecule, said method comprising the steps of:

a) synthesizing a plurality of substantially identical DNA molecules in a solution, wherein in said DNA molecules dye molecules are coupled onto at least part of the nucleotides (marked nucleotides);

b) extracting one of the synthesized DNA molecules by bonding it onto a fiber tip using the method as claimed in claim 1;

c) successively splitting off the nucleotides of the extracted DNA molecule individually in a detection apparatus; and d) detecting and identifying the individually split-off nucleotides in the detection apparatus.

11. A method for detecting an individual fluorescible molecule in a fluid, said method comprising the steps of:

passing the fluid through a microcapillary which has at one end an outlet with an internal diameter between approximately 300 and 700 nm and has a wall thickness at the outlet of less than one quarter of the excitation wavelength of the fluorescible molecule, wherein the fluorescible molecule exits at the outlet;

focusing a light beam of the excitation wavelength of the fluorescible molecule onto a region directly at the outlet of the microcapillary;

detecting the fluorescent light;

assuming a passage of the molecule through the focus as soon as the detected fluorescent light exceeds a predetermined intensity.

12. The method as claimed in claim 11, in which electrically charged fluorescible molecules are detected in the fluid, said passing step comprising the steps of:

dipping the microcapillary into a solution which is electrically coupled to an electrode;

forming, within the microcapillary, an electrical current path through the solution to a counter-electrode; and setting up an electrical voltage difference between the electrode and the counter-electrode such that the charged fluorescible molecules move out of the microcapillary through the outlet end.

13. A method for sequencing an individual DNA molecule, said method comprising the steps of:

a) synthesizing a plurality of substantially identical DNA molecules in a solution, wherein in said DNA molecules dye molecules are coupled onto at least a part of the nucleotides (marked nucleotides);

b) extracting one of the synthesized DNA molecules from the solution by binding onto a fiber;

c1) introducing the fiber tip into a microcapillary which has an internal diameter between approximately 300 and 700 nm. at one end;

c2) filling the microcapillary with a solution which effects a successive splitting off of individual nucleotides of the DNA molecule; and d) detecting and identifying the individual split-off and marked nucleotides at the end of the microcapillary.

14. The method as claimed in claim 13, wherein in step b) the DNA molecule is extracted as claimed in claim 1.

15. The method as claimed in claim 13, wherein the fiber tip in step c1) is positioned in the microcapillary in front of the outlet end.

16. The method as claimed in claim 13, wherein the individual marked nucleotides are detected as claimed in claim 11.

17. The method as claimed in claim 13, wherein different types of nucleotides are each marked with dyes having differing fluorescent lifetimes;

in step d) the marked nucleotides are detected by means of time-resolved fluorescence spectroscopy and are identified on the basis of the fluorescent lifetimes of the dyes coupled onto them.

18. The method as claimed in claim 13, wherein before step d) the steps as claimed in claim 12 are carried out.

19. An arrangement for carrying out the method as claimed in claim 11, said arrangement comprising:

a light source of a predetermined wavelength;

a microcapillary with an outlet with an internal diameter between approximately 300 and 700 nm. with a wall thickness less than one quarter of the predetermined wavelength, the light source being aligned with the end of the microcapillary so that its light is focused onto a test area which is formed in the region of the outlet and encompasses the entire cross-section of the outlet; and a means for detecting individual photons from the test area.

\* \* \* \* \*

UNITED STATES PATENT AND TRADEMARK OFFICE
CERTIFICATE OF CORRECTION

PATENT NO. : 6,225,068 B1  
DATED : May 1, 2001  
INVENTOR(S) : Wolfrum

Page 1 of 1

It is certified that error appears in the above-identified patent and that said Letters Patent is hereby corrected as shown below:

Title page,  
Item [30], Foreign Application Priority Data, please delete "197 42 227" and insert -- 197 42 227.6 --.

*Assistant Examiner,* please delete "Janell E. Taylor" and insert -- Janell Taylor Cleveland --.

Item [57],  
ABSTRACT,  
Line 2, please delete "then brounght into" and insert -- the brought into --.  
Line 4, please delete "the biotin" and insert -- The biotin --.  
Line 9, please delete "remvoded from" and insert -- removed from --.

Claim 1,  
Line 5, please delete "fluorescibel" and insert -- fluorescible --.  
Line 6, please delete "fluorescibel" and insert -- fluorescible --.

Claim 7,  
Line 3, after "5', please insert -- end --.

Claim 8,  
Line 2, please delete "fluorescibel" and insert -- fluorescible --.

Signed and Sealed this

Eighth Day of January, 2002

Attest:

JAMES E. ROGAN  
*Attesting Officer*  *Director of the United States Patent and Trademark Office*